United States Patent
Jallon

(10) Patent No.: US 9,801,569 B2
(45) Date of Patent: Oct. 31, 2017

(54) METHOD OF DETECTING ACTIVITY WITH A MOTION SENSOR, AND CORRESPONDING DEVICE AND COMPUTER PROGRAM

(71) Applicants: Commissariat a l'energie atomique et aux ene alt, Paris (FR); MOVEA, Grenoble (FR)

(72) Inventor: Pierre Jallon, Grenoble (FR)

(73) Assignees: Commissariat à l'énergie atomique et aux énergies alternatives, Paris (FR); MOVEA, Grenoble (FR)

( * ) Notice: Subject to any disclaimer, the term of this patent is extended or adjusted under 35 U.S.C. 154(b) by 738 days.

(21) Appl. No.: 14/353,193

(22) PCT Filed: Oct. 19, 2012

(86) PCT No.: PCT/FR2012/052394
§ 371 (c)(1),
(2) Date: Jul. 9, 2014

(87) PCT Pub. No.: WO2013/057447
PCT Pub. Date: Apr. 25, 2013

(65) Prior Publication Data
US 2014/0365163 A1 Dec. 11, 2014

(30) Foreign Application Priority Data
Oct. 21, 2011 (FR) ...................................... 11 59595

(51) Int. Cl.
*G01P 15/00* (2006.01)
*A61B 5/11* (2006.01)
(Continued)

(52) U.S. Cl.
CPC ........... *A61B 5/1123* (2013.01); *A61B 5/1116* (2013.01); *A61B 5/1118* (2013.01); *A61B 5/6823* (2013.01); *G01P 15/18* (2013.01)

(58) Field of Classification Search
CPC ......... G06K 19/0716; G06K 19/07749; G06K 7/10306; G06K 7/10564; G06K 9/00026;
(Continued)

(56) References Cited

U.S. PATENT DOCUMENTS

| | | | |
|---|---|---|---|
| 7,263,472 B2 * | 8/2007 | Porikli | ............... G06K 9/00335 382/103 |
| 2010/0001949 A1 * | 1/2010 | Shkolnikov | ........... G06F 1/1626 345/156 |

(Continued)

FOREIGN PATENT DOCUMENTS

WO 2010 122174 10/2010

OTHER PUBLICATIONS

Wang, L. et al. "Recent developments in human motion analysis" Pattern Recognition, vol. 36, pp. 585-601, 2003 XP 004393092.
(Continued)

*Primary Examiner* — Roy Y Yi
(74) *Attorney, Agent, or Firm* — Oblon, McClelland, Maier & Neustadt, L.L.P.

(57) ABSTRACT

This method for detecting activity (A) of a physical system carrying a motion sensor comprises the following steps: extracting (100) a sequence (M) of measurements provided by the motion sensor; deducing (102) therefrom an observation sequence (O) calculated on the basis of the measurement sequence (M); determining (104) the activity (A) of the physical system in the form of a sequence of states corresponding to the observation sequence, using a statistical model of components of the observation sequence in view of a plurality of possible predetermined states of the physical system.

(Continued)

Figure 1:
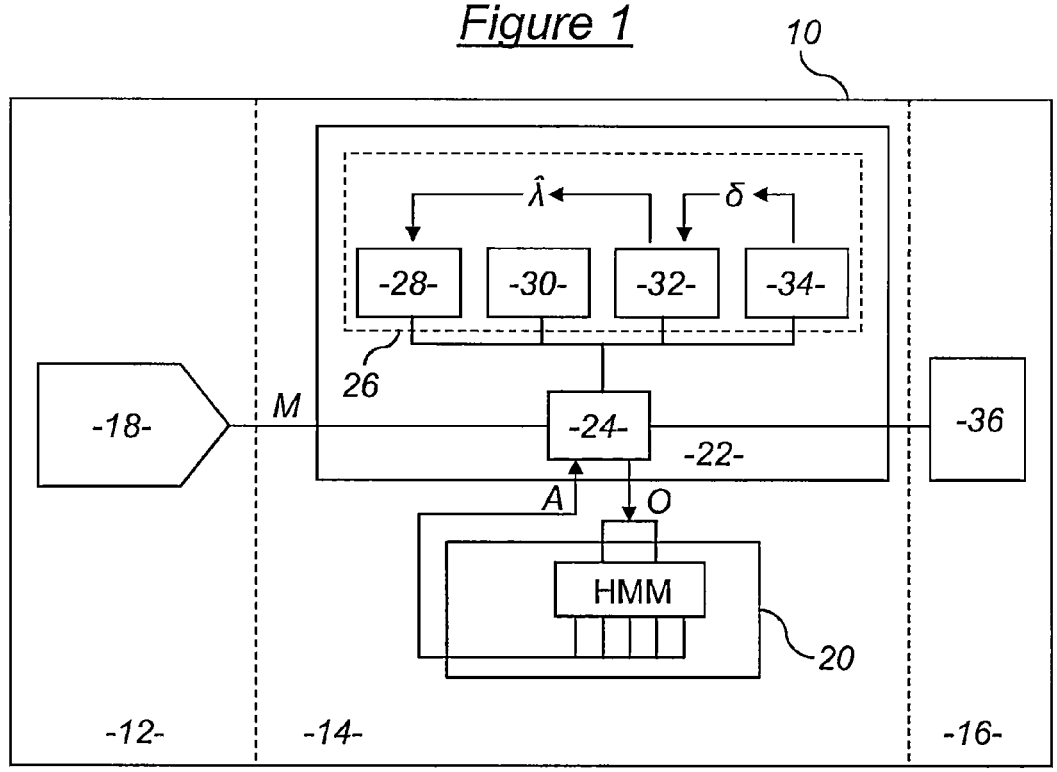

At least one component of the observation sequence (O) is calculated on the basis of a reference value ($\hat{\lambda}$) of a vector representing a reference axis. In addition, the method comprises the following calibration steps: calculation (106) of a likelihood value of the observation sequence (O) in view of said statistical model; comparison (106) of this likelihood value with a predetermined threshold; on the basis of this comparison, activating an estimation (108) of a new reference value ($\hat{\lambda}$) of the vector representing the reference axis.

13 Claims, 3 Drawing Sheets

(51) Int. Cl.
*A61B 5/00* (2006.01)
*G01P 15/18* (2013.01)

(58) Field of Classification Search
CPC .......... G06K 9/00087; G06K 9/00348; G06K 9/00369; G06K 9/00604; G06K 9/00711; G06K 9/00892; G06K 9/2027; G06K 9/22; G06K 9/46
See application file for complete search history.

(56) References Cited

U.S. PATENT DOCUMENTS

| | | |
|---|---|---|
| 2010/0010383 A1 | 1/2010 | Skelton et al. |
| 2011/0060215 A1* | 3/2011 | Tupin, Jr. ............ A61B 5/0507 600/425 |
| 2012/0143094 A1 | 6/2012 | Jallon |
| 2014/0229410 A1 | 8/2014 | Jallon et al. |

OTHER PUBLICATIONS

Bilmes, J.A. "A Gentle Tutorial of the EM Algorithm and its Application to Parameter Estimation for Gaussian Mixture and Hidden Markov Models" International Computer Science Institute, pp. 1-15, Apr. 1, 1998 XP 002594206.

Rabiner, L.R. et al. "An Introduction to Hidden Markov Models" IEEE ASSP Magazine, vol. 3, No. 1, Jan. 1986 XP 011353445.

Jallon, P. "A graph based algorithm for postures estimation based on accelerometers data" Proceedings of 2010 annual international conference of the IEEE EMBC, pp. 2778-2781 (4 pages), 2010.

International Search Report dated Jan. 4, 2013 in PCT/FR12/052394 Filed Oct. 19, 2012.

* cited by examiner

METHOD OF DETECTING ACTIVITY WITH A MOTION SENSOR, AND CORRESPONDING DEVICE AND COMPUTER PROGRAM

This invention relates to a method for detecting activity with a motion sensor. It also relates to a corresponding detection device and computer program.

More specifically, it relates to a method for detecting the activity of a physical system carrying a motion sensor, comprising the following steps:

- extracting a sequence of measurements provided by the motion sensor,
- deducing therefrom an observation sequence calculated using the sequence of measurements,
- determining the activity of the physical system in the form of a sequence of states corresponding to the observation sequence, using a statistical model of components of the observation sequence in view of a plurality of possible predetermined states of the physical system.

A method of this type is, for example, described in the article of P. Jallon, entitled "A graph based algorithm for postures estimation based on accelerometers data", published in Proceedings of 2010 Annual International Conference of the IEEE EMBC, pages 2778-2781. In this article, the sensor is an accelerometer with three measurement axes, worn on the body (waist or torso) of a person being observed: the accelerometer thus provides a sequence of measurements consisting of projections in the three axes thereof of a sum of the acceleration due to the earth's gravitational field and an acceleration specific to the sensor. These vector measurements with three components are not directly interpreted in order to determine the activity of the person being observed, but are first processed in order to separate the information associated with the gravitational acceleration from the information relating to the sensor-specific acceleration. Thus, three low-frequency components of an observation sequence are calculated by low-pass filtering of each vector measurement and three high-frequency components of the observation sequence are calculated by subtracting the three low-frequency components of the vector measurement. The resulting observation sequence is a sequence of vector values with six components. The first three are interpreted as indicating gravitational acceleration projections on the measurement axes of the sensor, so that they indicate the posture (sitting/standing or lying) of the person, while the following three are interpreted as indicating the acceleration specific to the sensor, so that they indicate the degree of activity (none, light, significant, etc.) of the person.

In addition, a statistical model of the components of the observation sequence is defined on the basis of a plurality of possible predetermined states of the person: sitting position, sitting/standing transition, static standing position, walking, standing/sitting transition. In consideration of the constraints of transitions from one state to another, these states are modeled as hidden states of a statistical Markov model and a classic method for analysis by Bayesian inference is applied to determine the activity of the person in the form of a sequence of states corresponding to the observation sequence.

Of course, this analysis method requires preliminary learning on known state sequences in order to define the parameters of the statistical model, in particular those of the laws of probability of observation associated with the different hidden states of the model.

This analysis method and the learning thereof also require calibration of the sensor, in particular in order to know its orientation in a predetermined reference posture such as the standing posture, for example. Then, the successful operation of the method requires that the sensor always be carried in the same way by the person being observed, although with a certain range of variations around the optimal positioning being tolerated. It is also assumed that the values learned under calibration do not vary from one person to another or from one experience to another, making this approximation both rough and restrictive.

Another method of this type is described in the international patent application published under number WO 2010/122174 A1. The same sequence of measurements is obtained from an accelerometer, and an observation sequence of which the values are vector values having four components is deduced therefrom. The first three components correspond to those obtained in the aforementioned article, while the fourth component is the norm of the output of a high-pass filter applied to the measurements sequence. As above, the activity of the person being observed is determined in the form of a sequence of states corresponding to the observation sequence by means of a predefined statistical model. Also as above, the method requires learning and calibration and has the same disadvantages.

It may thus be desirable to provide an activity detection method that makes it possible to overcome at least some of the aforementioned problems and constraints.

The invention therefore relates to a method for detecting activity of a physical system carrying a motion sensor, comprising the following steps:

- extracting a sequence of measurements provided by the motion sensor,
- deducing therefrom an observation sequence calculated using the sequence of measurements,
- determining the activity of the physical system in the form of a sequence of states corresponding to the observation sequence, using a statistical model of components of the observation sequence in view of a plurality of possible predetermined states of the physical system, wherein at least one component of the observation sequence is calculated on the basis of a reference value of a vector representing a reference axis, the method comprising the following calibration steps:

- calculating a likelihood value for the observation sequence in view of said statistical model,
- comparing this likelihood value with a predetermined threshold,
- on the basis of this comparison, activating an estimation of a new reference value for the vector representing the reference axis of the motion sensor.

Thus, by making at least one component of the observation sequence explicitly dependent on a vector reference value indicating a preferred direction and providing means enabling this reference value to be reconsidered on the basis of a likelihood test that can be executed during the observation of the system, the method is made capable of performing a calibration at any time. This method is thus rendered less sensitive to how the sensor is carried by the physical system and more robust with respect to any change in the system observed, experience or arrangement of the motion sensor during an observation.

Optionally, the reference axis can be estimated, via its representative vector, by means of measurements provided by the motion sensor. Thus, the calibration can be performed automatically and autonomously owing to the motion sensor.

Also optionally, a method according to the invention can further comprise a step of invalidating at least some of the sequence of states corresponding to the observation sequence, on the basis of the likelihood value.

This makes it possible not to take into account the determination of an activity, at least in part, when the latter is obtained from observations for which the reference value is not representative of the reference axis.

Also optionally, the observation sequence is deduced from the measurement sequence in the following way:
  calculation of a first component, on the basis of a possible decimation of the measurement sequence, a low-pass filtering with a predetermined cutoff frequency, for example 0.125 Hz, of each component of the sequence of measurements possibly decimated, then a projection of the resulting components on the reference value,
  calculation of at least one second component, on the basis of a possible decimation of the measurement sequence, then a band-pass filtering with predetermined cutoff frequencies, for example a low cutoff frequency of 0.125 Hz and a high cutoff frequency of 0.75 Hz, of each component of the measurement sequence possibly decimated.

Also optionally, the statistical model is a single Markov model with hidden states, each hidden state of which corresponds to one of the possible predetermined states of the physical system, the law of conditional probability of the observation of each hidden state being modeled by a sum of normal laws.

Also optionally, the calibration comprises:
  the calculation of the value V of the likelihood of the observation sequence in view of said statistical model in the form:

$$V = \frac{1}{N}\log(p(O_{1:N})),$$

where N is the number of observation samples in the observation sequence, $O_{1:N}$ designating the N successive samples,
  a comparison of this likelihood value with a predetermined threshold, this threshold being defined on the basis of the random drawing of a plurality of theoretical observation sequences based on said statistical model, and
  the activation of the estimation of a new reference value for the vector representing the reference axis only if the likelihood value is lower than the predetermined threshold.

Also optionally:
  at least one component of the observation sequence is calculated independently of the reference value of the vector representing the reference axis,
  at least one state of the physical system corresponding to a measurement sequence is detected on the basis of this observation sequence component independent of the reference value,
  the new reference value is estimated on the basis of the measurement sequence corresponding to this state detectable on the basis of the observation sequence component independent of the reference value.

Also optionally, the estimation of a new reference value of the vector representing the reference axis comprises steps consisting of:
  detecting and recovering, on the basis of said at least one observation sequence component independent of the reference value, a measurement sequence corresponding to a predetermined state wherein the vector representing the reference axis must have, on average, the reference value in consideration of said statistical model,
  calculating the average values of the components of said representative vector in this measurement sequence corresponding to the predetermined state, for example by possible decimation of the measurement sequence corresponding to the predetermined state, low-pass filtering with a predetermined cutoff frequency, for example, 0.125 Hz, of each component of this measurement sequence possibly decimated, then calculating the averages of the filtered components, and
  assigning these average values to the new reference value.

The invention also relates to the application of a detection method as defined above to the observation, by means of a three-dimensional accelerometer, of a person capable of being located, at each instant, in one of the following predetermined states: a "sitting position" state, a "sitting/standing transition" state, a "static standing position" state, a "walking" state, and a "standing/sitting transition" state; the reference value being the value, in the frame of the measurement axes of the three-dimensional accelerometer, of the components of a vertical downward-oriented unit vector when the person being observed is wearing the three-dimensional accelerometer and is in the "static standing position" or "walking" state.

The invention also relates to a device for detecting the activity of a physical system comprising:
  a motion sensor intended to be carried by the physical system in order to provide a sequence of measurements,
  means for storing a statistical model associating possible values of observation sequence components with a plurality of possible predetermined states of the physical system,
  a calculator, connected to the motion sensor and to the storage means, programmed to calculate an observation sequence on the basis of the measurement sequence and to determine, using the statistical model, the activity of the physical system in the form of a sequence of states corresponding to the observation sequence,
wherein the calculator is programmed to calculate at least one component of the observation sequence on the basis of a reference value of a vector representing a reference axis, the device comprising calibration means designed to:
  calculate a likelihood value for the observation sequence in view of said statistical model,
  compare this likelihood value with a predetermined threshold,
  activate an estimation of a new reference value for the vector representing the reference axis on the basis of this comparison.

Optionally, the motion sensor is an accelerometer with three measurement axes, the reference axis estimable by means of the measurements provided by the motion sensor being the axis of the earth's gravitational field, the reference value of a vector representing this axis being calculated on the basis of an estimation of the coordinates of an acceleration due to the earth's gravitational field in the frame of reference of the measurement axes of the accelerometer when the physical system is in a predetermined state.

The invention also relates to a system for detecting the activity of a physical system, comprising:
- a belt intended to be worn on the torso or the waist of a person, and
- a housing secured to the belt and comprising a detection device as defined above.

Finally, the invention also relates to a computer program that can be downloaded from a communication network and/or recorded on a computer-readable medium and/or run by a processor, comprising instructions for carrying out the steps of a detection method as defined above, when said program is run on a computer.

Figure 2:
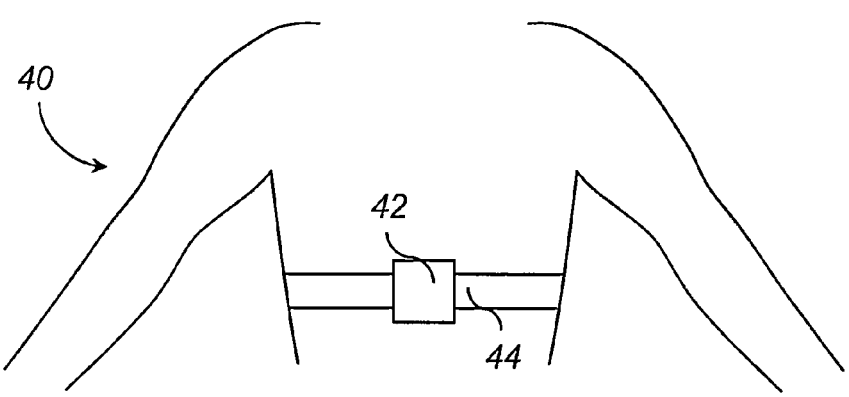
Figure 3:
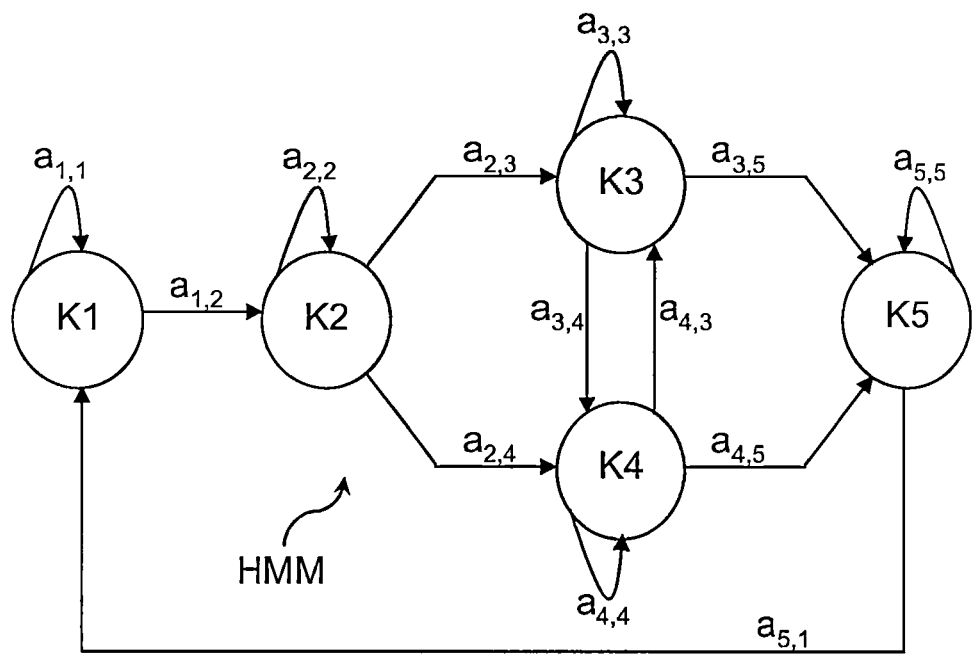
Figure 4:
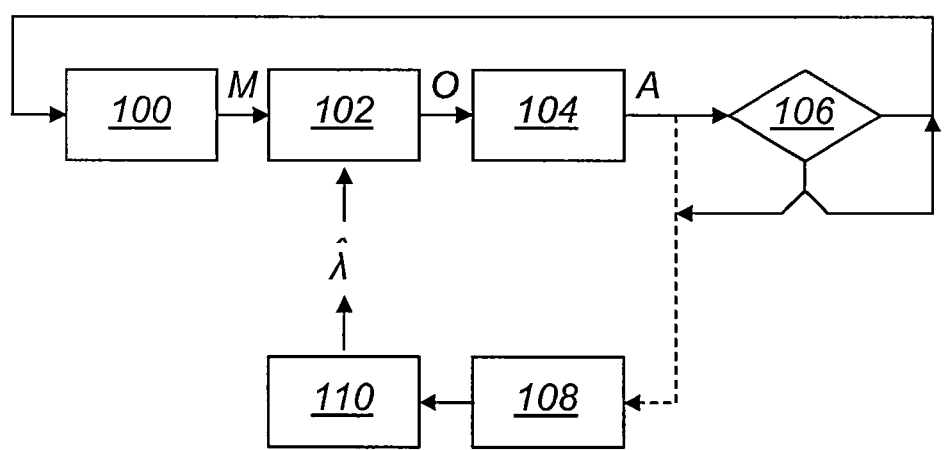
Figure 5:
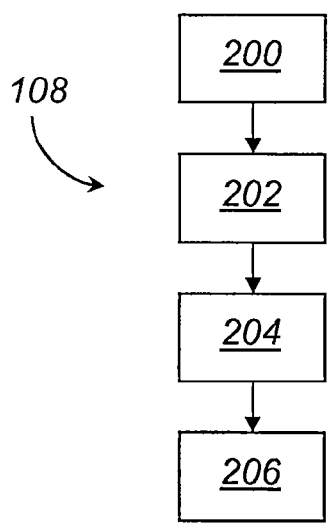
Figure 6:
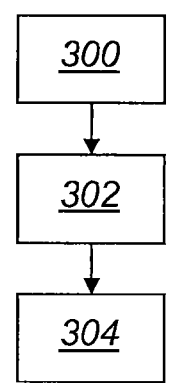
Figure 7:
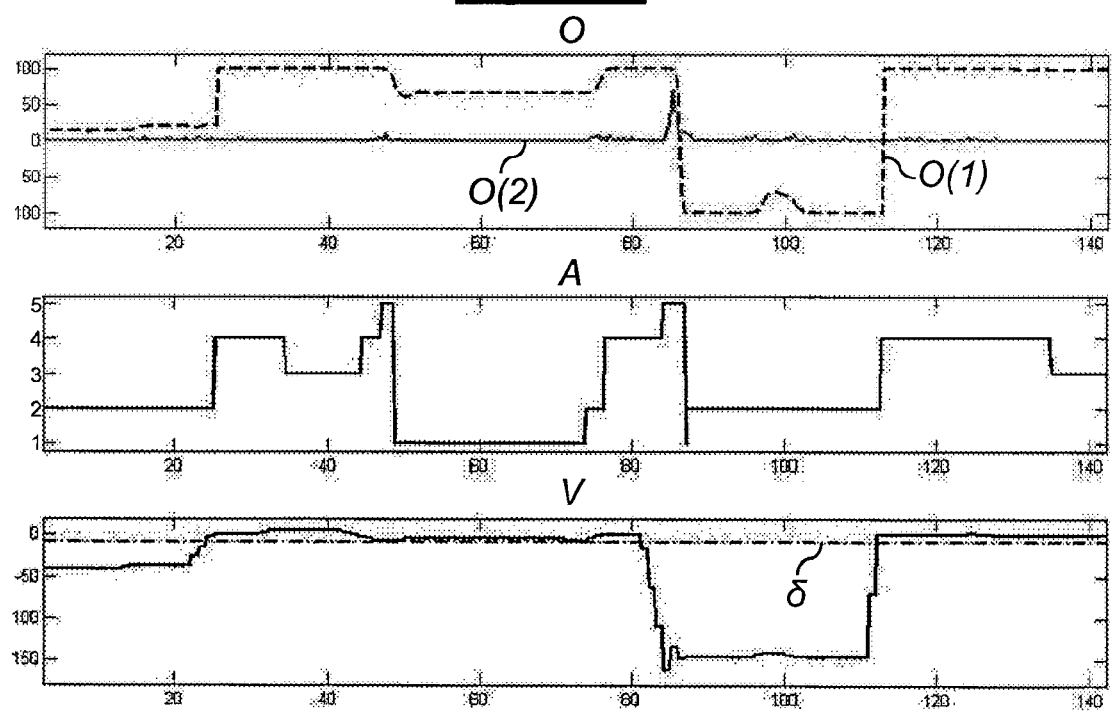

The invention will be better understood in view of the following description, provided solely as an example, and with reference to the appended drawings, wherein:

FIG. 1 schematically shows the general structure of a detection device according to an embodiment of the invention, FIG. 2 shows a specific use of the detection device of FIG. 1, FIG. 3 shows an example of a statistical Markov model with hidden states having transition constraints between hidden states and capable of being taken into account by the detection device of FIG. 1, FIG. 4 shows the successive steps of a detection method according to an embodiment of the invention, FIG. 5 shows the detail of a calibration step of the method of FIG. 4, FIG. 6 shows the successive steps of a method for calculating a threshold parameter taken into account in the method of FIG. 4, and FIG. 7 shows a set of three time diagrams of intermediate or output data of the device of FIG. 1 implementing the method of FIG. 4.

The device 10 shown in FIG. 1 is a device for detecting the activity of a physical system observed by at least one sensor. It comprises, to this end, a measurement module 12, a processing module 14 and an interface module 16.

The measurement module 12 comprises one or more sensors, comprising at least one motion sensor, represented by the single reference 18 for the observation of the physical system.

In a non-limiting manner, the sensor 18 can, for example, comprise a motion sensor with one, two or three measurement axes, in particular a three-dimensional accelerometer worn by a person, in order to determine the activity of said person in the form of a sequence of attitudes among a plurality of possible attitudes capable of occurring in succession (for example, sitting, standing, sitting/standing or standing/sitting transition, walking).

More generally, it can comprise a motion sensor for determining the activity of a mobile physical system in the form of a sequence of states among a plurality of predetermined states capable of occurring in succession.

The motion sensor 18 can also comprise a plurality of sensors each providing measurements that, combined, make it possible to envisage detecting more complex situations.

It takes measurements of the physical system in order to provide a measurement signal, transmitted in the form of a sequence M of measurement data to the processing module 14. The measurement data is obtained directly from a sampling of the measurement signal, for example 100 or 200 Hz. In the case of a three-dimensional accelerometer, each measurement data sample is a three-component vector, each component representing the projection of the total acceleration measured by the sensor on one of its three measurement axis. This total acceleration comprises the earth's gravitational acceleration and the acceleration specific to the motion sensor 18.

The motion sensor 18 also has the property of enabling, by means of the measurements that it provides a reference axis to be estimated, represented by a reference vector λ, for example of norm 1, indicating its direction and its sense. As will be described in detail below, the coordinates of this reference vector can be expressed in the frame of reference of the motion sensor 18 and have a particular reference value $\hat{\lambda}=(\hat{\lambda}_x,\hat{\lambda}_y,\hat{\lambda}_z)$ when the motion sensor 18 is in a predetermined and preferred orientation corresponding, for example, to at least one of the possible states of the physical system. In the case of an accelerometric sensor worn by a person, the reference axis is advantageously the axis of the earth's gravitational field.

The processing module 14 is an electronic circuit, in particular that of a computer. It comprises storage means 20, for example a RAM, a ROM or another type of memory, wherein the parameters of at least one statistical model are stored, for example an HMM hidden-state Markov model.

In general, this statistical model stored in the memory 20, or the structured assembly of these statistical models if a plurality of them are combined, associates a succession of possible observation data values with a succession of states corresponding to at least some of the hidden states of the statistical model HMM and identifying the possible states of the physical system carrying the motion sensor 18.

The processing module 14 also comprises a calculator 22, for example a central computer unit equipped with a microprocessor 24 and a storage space for at least one computer program 26. This calculator 22, and more specifically the microprocessor 24, is connected to the motion sensor 18 and to the memory 20.

The computer program 26 performs four main functions illustrated by modules 28, 30, 32 and 34 in FIG. 1.

The first main function, performed by a filtering module 28, is a function for transforming the measurement sequence M provided by the motion sensor 18 into an observation sequence O capable of being checked against the statistical model HMM stored in the memory 20. Like the measurement sequence M, the observation sequence O is formed by a succession of samples, each of these samples being capable of being a vector, each component of which results from a specific processing of the measurement sequence M. In general, according to the invention, at least one component of each sample of the observation sequence O is calculated on the basis of the reference value λ.

As a non-limiting example, when the motion sensor 18 is a three-dimensional accelerometer worn by a person whose activity is to be determined in the form of a sequence of predetermined possible attitudes of the person (comprising: sitting position, sitting/standing transition, static standing position, walking, standing/sitting transition), the sequence M is a sequence of acceleration vectors $\gamma_n=\gamma_n^g+\gamma_n^p$, n designating the time index of the samples, $\gamma_n^g$ the low-frequency part of these acceleration vectors corresponding to the acceleration due to the earth's gravitational field capable of being obtained by a simple low-pass filtering and $\gamma_n^p$ the high-frequency part of these acceleration vectors corresponding to the acceleration specific to the sensor capable of being obtained by a simple pass-band filtering. These vectors are known by their components projected in the three measurement axes of the motion sensor 18.

The filtering module 28 can thus separate these two parts $\gamma_n^g$ and $\gamma_n^p$ and provide an observation sequence O with two components:

a first sequence of components $O_n(1)$, obtained by decimation at 5 Hz of the measurement sequence M, low-pass filtering of the resulting samples with a cutoff frequency of 0.125 Hz, then normalized projection of the vector $\gamma_n^g$ thus obtained on the reference value $\hat{\lambda}$, a second sequence of components $O_n(2)$, obtained by decimation at 5 Hz of the measurement sequence M, band-pass filtering of the resulting samples with a low cutoff frequency of 0.125 Hz and a high cutoff frequency of 0.75 Hz, then calculation of the norm of the vector $\gamma_n^g$ thus obtained.

More specifically, and as an example:

$$O_n(1) = 100 \cdot \frac{\langle \gamma_n^g, \hat{\lambda} \rangle}{\|\gamma_n^g\|},$$

where $\langle , \rangle$ designates the scalar product and $\| \|$ the Euclidean norm, $$O_n(2) = 1 \, 0 \|\gamma_n^p\|.$$

It is thus noted that the first component $O_n(1)$ of each sample of the observation sequence O is calculated on the basis of the reference value $\hat{\lambda}$ while the second component $O_n(2)$ is independent of this reference value.

The second main function, performed by an activity detection module 30, for example in the form of an instruction loop, is a function of detecting a sequence of possible predetermined states of the physical system, on the basis of a sequence O of observation data provided by the filtering module 28. More specifically, the activity detection module 30 is programmed to enable the microprocessor 24 to provide an activity A in the form of a sequence of states by processing the observation sequence O by means of the statistical model HMM stored in the memory 20.

The third main function, performed by a test module 32 is a function of calculating a likelihood value of the observation sequence O in view of the model HMM stored in the memory 20 and of comparison of this likelihood value with a threshold $\delta$ for a possible update of the reference value $\hat{\lambda}$.

Finally, the fourth main function, performed by a threshold calculation module 32, is a function of calculating the threshold value $\delta$ for the HMM model considered.

The interface module 16 has an interface 36 making it possible to display the result of a detection performed by the microprocessor 24, for example in the form of a time diagram of the successive states corresponding to the observation O. As one of the possible benefits of the detection device 10 is optionally also to detect a predetermined critical situation, this interface 36 can in particular comprise an alert activator. The interface 36 or its alert activator can, for example, comprise a screen for displaying results or a warning message, a loudspeaker for emitting a sound signal or a transmitter for transmitting a signal to a remote alarm. The alert activator can be activated upon detection of one or more particular activity or activities. An example of a detectable event/activity capable of activating an alert is, for example, a fall.

It should be noted that the observation 12, processing 14 and interface 16 modules are structurally separable. Thus, the detection device 10 can be designed in one piece or in multiple distinct hardware pieces connected to one another by wire or wireless data transmission means. In particular, the processing 14 and optionally interface 16 modules can be implemented by a computer. Only the observation module 12 is necessarily in the vicinity or even in contact with the physical system observed since it comprises the sensor(s) 18.

In FIG. 2, a particularly compact embodiment is shown, for use in monitoring the activity of a person 40. According to this embodiment, the detection device 10 of FIG. 1 is entirely integrated in a housing 42 worn by the person 40. The sensor is a three-dimensional accelerometer and there are, for example, five successive attitudes characteristic of the activity of the person 40: a "sitting position" attitude, a "sitting/standing transition" attitude, a "static standing" attitude, a "walking" attitude and a "standing/sitting transition" attitude, each of these attitudes being represented by a hidden state corresponding to a single Markov model HMM. For this application, the housing 42 is, for example, firmly held on the torso or waist of the person 40 by means of a belt 44.

An example of a statistical model HMM capable of being stored in the memory will now be described in detail in reference to FIG. 3, for the application mentioned above. This model HMM is a hidden-state Markov model, each hidden state of which corresponds to one of the five attitudes mentioned above. It is defined by the following parameters:

the number of hidden states of this model HMM, equal to 5 in the example of FIG. 3, $\pi_1, \ldots, \pi_5$, the five initial probabilities, independent of any observation, of each hidden state of this model HMM, for example all equal to 0.2, $(a_{i,j})_{1 \leq i, j \leq 5}$, the matrix of probabilities of transition of each hidden state i to each other hidden state j of this model HMM, and for each hidden state, the parameters of a law of probability of the observation provided at each instant at the input of this model.

The hidden states of the model HMM of FIG. 3 are thus the following: K1 for the "sitting position" state, K2 for the "sitting/standing transition" state, K3 for the "static standing position" state, K4 for the "walking" state and K5 for the "standing/sitting transition" state.

It is also noted that this model imposes certain impossible transition constraints, such as, for example, the transition from the "static standing position" to the "sitting position" state, which cannot be performed directly without going through the "standing/sitting transition" state. This results, for example, in the following matrix of transition probabilities:

$$(a_{i,j})_{5 \times 5} = \begin{pmatrix} 1-\varepsilon & \varepsilon & 0 & 0 & 0 \\ 0 & 1-\varepsilon & \varepsilon/2 & \varepsilon/2 & 0 \\ 0 & 0 & 1-\varepsilon & \varepsilon/2 & \varepsilon/2 \\ 0 & 0 & \varepsilon/2 & 1-\varepsilon & \varepsilon/2 \\ \varepsilon & 0 & 0 & 0 & 1-\varepsilon \end{pmatrix},$$

where the variable $\varepsilon$ is, for example, between $10^{-2}$ and $10^{-4}$.

In FIG. 3, only the non-zero transition probabilities are shown.

The laws of probability of observation at each instant and for each hidden state are defined by parameters that are of course dependent upon the reference value $\hat{\lambda}$ arbitrarily chosen. For example, in the application described above, the reference vector $\lambda$ is a vertical unit vector oriented downward in the terrestrial reference frame, the reference value $\hat{\lambda}$ being the value of the components of this reference vector $\lambda$ in the coordinates of the frame of the measurement axes of the three-dimensional accelerometer when it is worn by the person being observed and when the person is in the "static standing position" state K3. By choosing such a reference value $\hat{\lambda}$, it is possible to initialize it to a first value obtained by calibration, taking a series of measurements when the person being observed is wearing the motion sensor 18 and is in the static standing position. $\hat{\lambda}$ then corresponds in effect to the measured acceleration vector that must simply be averaged over the series measured. More generally, it is advantageous to choose a reference value that can be deduced directly from the measurements associated with one of the predetermined states. It should also be noted that it is possible to initialize $\hat{\lambda}$ to an arbitrary value without calibration.

Any one of the laws of conditional probability of observation knowing the state to be determined can be chosen from the family of normal laws. A normal law is defined by its expectation $\mu$ and its variance $\Sigma$. When the data provided at the input of the model HMM is multi-valued, $\mu$ is a vector comprising as many components and $\Sigma$ is a matrix comprising as many rows and columns as values provided at each instant at the input of the model HMM.

In the above-mentioned example, as the observation sequence has two components, $\mu$ is a vector with two components and $\Sigma$ is a 2×2 matrix. Also in the above-mentioned example, each law of conditional probability of observation knowing the state to be determined is, in practice, advantageously a sum of two normal laws capable of being written in the form:

$$p(O_n \mid A_n = i) = \sum_{j=1}^{2} c_{i,j} \frac{1}{\sqrt{2\pi}^{3/2} |\Sigma_{i,j}|^{1/2}} \exp\left(-\frac{1}{2}(O_n - \mu_{i,j})^T \sum_{i,j}^{-1} (O_n - \mu_{i,j})\right),$$

where the parameters $c_{i,j}$, $\mu_{i,j}$ and $\Sigma_{i,j}$ are, for example, defined as indicated by the following table:

| State Ki | $c_{i,1}$ | $\mu_{i,1}$ | $\Sigma_{i,1}$ | $c_{i,2}$ | $\mu_{i,2}$ | $\Sigma_{i,2}$ |
|---|---|---|---|---|---|---|
| i = 1 | 0.424 | $\begin{bmatrix} 78.28 \\ 0.0059 \end{bmatrix}$ | $\begin{bmatrix} 17.72 & 0.024 \\ 0.024 & 0.0177 \end{bmatrix}$ | 0.576 | $\begin{bmatrix} 95.072 \\ 0.0085 \end{bmatrix}$ | $\begin{bmatrix} 16.40 & -0.016 \\ -0.016 & 0.0164 \end{bmatrix}$ |
| i = 2 | 0.308 | $\begin{bmatrix} 85.26 \\ 1.5033 \end{bmatrix}$ | $\begin{bmatrix} 71.25 & 4.99 \\ 4.99 & 4.36 \end{bmatrix}$ | 0.692 | $\begin{bmatrix} 99.37 \\ 0.461 \end{bmatrix}$ | $\begin{bmatrix} 0.496 & -0.155 \\ -0.155 & 0.51 \end{bmatrix}$ |
| i = 3 | 0.950 | $\begin{bmatrix} 99.73 \\ 0.0044 \end{bmatrix}$ | $\begin{bmatrix} 0.078 & 0.000067 \\ 0.000067 & 0.0001 \end{bmatrix}$ | 0.050 | $\begin{bmatrix} 99.82 \\ 0.137 \end{bmatrix}$ | $\begin{bmatrix} 0.016 & -0.00045 \\ -0.00045 & 0.0135 \end{bmatrix}$ |
| i = 4 | 0.083 | $\begin{bmatrix} 99.33 \\ 1.61 \end{bmatrix}$ | $\begin{bmatrix} 0.133 & -0.09 \\ -0.09 & 2.69 \end{bmatrix}$ | 0.916 | $\begin{bmatrix} 99.9 \\ 1.567 \end{bmatrix}$ | $\begin{bmatrix} 0.0098 & 0.021 \\ 0.021 & 2.36 \end{bmatrix}$ |
| i = 5 | 0.190 | $\begin{bmatrix} 93.62 \\ 3.04 \end{bmatrix}$ | $\begin{bmatrix} 57.98 & -2.44 \\ -2.44 & 4.16 \end{bmatrix}$ | 0.810 | $\begin{bmatrix} 93.31 \\ 0.22 \end{bmatrix}$ | $\begin{bmatrix} 48.61 & -0.02 \\ -0.02 & 0.08 \end{bmatrix}$ |

The operation of the detection device 10 will now be described in detail in reference to FIG. 4. More specifically, the execution of the filtering module 28, the activity detection module 30 and the test module 32 by the microprocessor 24 produces the sequence of steps illustrated in this figure.

In a first step 100, the motion sensor 18, in this particular case the three-dimensional accelerometer, transmits a sequence M of measurement data to the calculator 22. This data is vector data with three components indicating the projection of the acceleration measured on each measurement axis of the motion sensor 18.

In a step 102, during reception 100 of the successive data transmitted by the motion sensor 18, the microprocessor 24 of the calculator 22 launches the execution of the filtering module 28 as described above, to produce a sequence of N observation data items denoted $O_{1:N} = \{O_1, \ldots O_N\}$, wherein each sample $O_n$ is a vector with two components $O_n(1)$ and $O_n(2)$ as defined above.

In the next step 104, the microprocessor 24 of the calculator 22 launches the execution of the activity detection software module 30. By means of the statistical model HMM mentioned above, the activity of the person wearing the motion sensor 18 is determined in the form of a sequence of states (or a sequence of attitudes) corresponding to the observation sequence $O_{1:N}$. This sequence of states is denoted $\hat{A}_{1:N} = \{\hat{A}_1, \ldots \hat{A}_N\}$, wherein each sample $\hat{A}_n$ is a natural integer between 1 and 5 identifying one of the five states of the model ("sitting position", "sitting/standing transition", "static standing position", "walking", "standing/sitting transition"). In consideration of the hidden state Markov model HMM chosen:

$$\hat{A}_{1:N} = \underset{A_{1:N}}{\operatorname{argmax}}\ [p(A_{1:N} \mid O_{1:N})]$$

$$= \underset{A_{1:N}}{\operatorname{argmax}}\ [p(A_{1:N}, O_{1:N})/p(O_{1:N})]$$

$$= \underset{A_{1:N}}{\operatorname{argmax}}\ [p(A_{1:N}, O_{1:N})],$$

with:

$$p(A_{1:N}, O_{1:N}) = p(A_1)p(O_1 \mid A_1) \prod_{n=2}^{N} p(A_n \mid A_{n-1})p(O_n \mid A_n).$$

Classically, the sequence of states $\hat{A}_{1:N}$ is estimated by means of a Viterbi algorithm.

Then, in a step 106, the microprocessor 24 of the calculator 22 launches the execution of the test module 32 in order to calculate a likelihood value V of the observation sequence $O_{1:N}$ in view of the statistical model HMM. The likelihood value V is, for example, given by the following formula:

$$V = \frac{1}{N}\log(p(O_{1:N})),$$

wherein the expression $p(O_{1:N})$ is developed in the form:

$$p(O_{1:N}) = \sum_{A_1=1}^{M} \cdots \sum_{A_N=1}^{M} p(O_{1:N}, A_{1:N})$$

$$= \sum_{A_1=1}^{M} \cdots \sum_{A_N=1}^{M} p(A_1)p(O_1 | A_1) \prod_{n=2}^{N} p(A_n | A_{n-1})p(O_n | A_n),$$

where M is the number of states, i.e. 5 in the example considered. N is for example equal to 10 or 20.

In view of the laws of probability mentioned above, this likelihood value V can be calculated directly without any particular difficulty. It is higher as the reference value $\hat{\lambda}$ remains adapted to the observation in progress. Indeed, the situation may have changed since the initialization of the reference value or since its last update, due to a change in the position of the accelerometric sensor on the body of the person being observed, due to a change in the person being observed or due to another disruptive event. In this case, the likelihood value V can be degraded. It is therefore beneficial to regularly verify that this value remains greater than a predetermined threshold denoted δ. This threshold δ is dependent only on the model HMM stored in the memory 20 and a method for calculating its value will be described in detail in reference to FIG. 6. In consideration of the numeric parameters of the model HMM described above, the method shown in FIG. 6 provides the value δ=−8.

In step 106, the likelihood value V is compared to the threshold value δ. If V>δ, the method returns directly to step 100 to process a new measurement sequence. Otherwise, the method activates a step 108 of updating the reference value $\hat{\lambda}$ before returning to step 100.

The updating step 108 is performed in parallel with the loop of steps 100 to 106 and is based on sequences of successive states provided at the output of step 104. In the example considered, it is based on the detection of a state wherein a sufficient proper acceleration is measured for a minimal duration. In effect, this proper acceleration is detected by the second component of the samples of the observation sequence, which is independent of the reference value $\hat{\lambda}$ and therefore insensitive to its drifts. In addition, by imposing a minimal duration, for example 12 seconds, the walking state is distinguished from the sitting/standing transition or standing/sitting transition states, which do not last as long and which are the only ones, with the walking state, to have a sufficient proper acceleration. Thus, independently of the reference value $\hat{\lambda}$, it is possible to detect precisely when the person being observed is in the walking state. However, this walking state is also a state wherein, as in the static standing position state, the low-frequency portion of the acceleration vector measured must be, on average, co-linear to the reference vector λ in order for the statistical model to be applied optimally, as was defined in the construction of the model.

Thus, step 108 consists, as shown in FIG. 5, in:
detecting (200) a sequence of successive observation data, during which a sufficient proper acceleration is measured over a duration greater than a predefined minimal duration (for example 12 seconds),
recovering (202) the corresponding measurement sequence, truncating this sequence by a few seconds at the beginning and at the end so as to be sure that only a walking sequence is preserved,
on this truncated measurement sequence, performing (204) a decimation at 5 Hz, then a low-pass filtering of the resulting samples with a cutoff frequency of 0.125 Hz,
calculating (206) the average on the truncated sequence of each vector component measured and filtered, and assigning this average to the corresponding component of the reference value $\hat{\lambda}$.

To detect a sufficient proper acceleration (even denoted, for example, ACC, the opposite even then being denoted $\overline{ACC}$), it is possible to astutely define two new posterior probability laws for the second observation component $O_n(2)$:

$$p(O_n(2) | ACC) = \frac{1}{\sqrt{2\pi}^{1/2} \sigma_{ACC}^{1/2}} \exp\left(-\frac{(O_n(2) - \mu_{ACC})^2}{2\sigma_{ACC}^2}\right),$$

with, for example, $\mu_{ACC}$=1.282134 and $\sigma_{ACC}$=1.09, and $$p(O_n(2) | \overline{ACC}) = \frac{1}{\sqrt{2\pi}^{1/2} \sigma_{\overline{ACC}}^{1/2}} \exp\left(-\frac{(O_n(2) - \mu_{\overline{ACC}})^2}{2\sigma_{\overline{ACC}}^2}\right),$$

with, for example, $\mu_{\overline{ACC}}$=0.008 and $\sigma_{\overline{ACC}}$=0.045.

It is then decided at each instant (i.e. for each sample) that the proper acceleration is sufficient if:

$$\frac{p(O_n(2) | ACC)}{p(O_n(2) | ACC) + p(O_n(2) | \overline{ACC})} > 0.8.$$

It is therefore necessary for this condition to be verified for at least 12 seconds in order for the update of the reference value $\hat{\lambda}$ to be capable of being performed.

Step 108 is optionally but advantageously followed by a step 110 of invalidating the activity determined, at least partially by invalidation of at least some of the sequence of states determined on the basis of the observation sequence in step 104. More specifically, the states determined for which the likelihood value is less than the threshold value δ can be invalidated. Also optionally, information can be generated making it possible to warn the user that an activity has been determined even though the likelihood value was low. This information can be displayed by the interface 36.

The method for calculating the threshold value δ, illustrated in FIG. 6, comprises a first step 300 involving a random drawing of a large number of theoretical observation sequences on the basis of the observation model defined above, for example at least 1000. Practically speaking, to perform this random drawing, for each theoretical observation sequence, a first initial state $A_1$ is randomly drawn, then an observation value according to the law $p(O|A_1)$ is randomly drawn. This is performed iteratively until the Nth observation value by randomly drawing the next state according to the transition laws defined for the model HMM, then the next observation value according to the law, which corresponds to the performance of this next state.

Then, in a step 302, the likelihood value V is calculated for each of the theoretical observation sequences obtained in step 300.

Finally, in a last step 304, the value of δ is determined so that, for example, 95% of the likelihood values V calculated in step 302 are greater than this value δ. In particular, as indicated above, this gives δ=−8 for the model described above and illustrated in FIG. 3.

Three examples of time diagrams of intermediate or output data of the device of FIG. 1 implementing the detection method of FIG. 4 are shown in FIG. 7.

The first diagram provides an example O of an observation data sequence with two components as defined above. The sequence of the first components $O_n(1)$ is denoted $O(1)$ and the sequence of the second components $O_n(2)$ is denoted $O(2)$.

The second diagram provides the resulting activity A estimated by the activity detection module 30 in the form of a sequence of states: on the y-axis of this diagram, 1 identifies the sitting position state (hidden state K1), 2 identifies the sitting/standing transition state (hidden state K2), 3 identifies the static standing position state (hidden state K3), 4 identifies the walking state (hidden state K4) and 5 identifies the standing/sitting transition state (hidden state K5).

The third diagram provides a resulting sequence of likelihood values V, estimated by the test module 32 in sliding windows. The likelihood values V are compared at each instant to the threshold δ.

It is noted, in the first and third diagrams, that until around the 25th sample, the reference value $\hat{\lambda}$ appears to be poorly adapted to the model since a sitting/standing transition state is detected for an excessive duration, confirmed by the likelihood value V<δ.

After the detection of a sufficiently long proper acceleration period measured between the 15th and 25th samples (cf. curve O(2)), the reference value $\hat{\lambda}$ is updated toward the 25th sample, confirmed by the likelihood value V>δ after this instant.

It is then noted that, after another proper acceleration period between the 75th and 80th samples, during which the motion sensor 18 must have been inadvertently moved, the likelihood value again goes below the threshold δ.

The situation is reestablished around the 112th sample, after the detection of a new sufficiently long proper acceleration period (cf. curve O(2)), when the reference value $\hat{\lambda}$ is again updated, confirmed by the likelihood value V>δ after this instant.

It is noted that the decisions made while V<δ could alternatively not be indicated in the activity sequence A. It is also noted that this activity sequence A could be directly displayed, or represented in one way or another, on the interface 36.

It appears clearly that a detection device such as that described above is capable of detecting drifts in the estimation of the states observed and consequently being automatically calibrated. It is therefore more robust than similar devices of the prior art.

It should also be noted that the invention is not limited to the embodiment described above.

In particular, the reference value $\hat{\lambda}$ is not necessarily that defined above, namely the value, in the frame of the measurement axes of the three-dimensional accelerometer 18, of the components of a unit vector, vertical and oriented downward when the person being observed is wearing the three-dimensional accelerometer and is in the "static standing position" state. This reference value is of course very closely linked to the application chosen as a non-limiting example.

More generally, the reference value is the value, in a frame associated with the motion sensor 18, of the components of a reference vector that can be estimated by means of the measurements provided by the sensor when the physical system being observed is in a predetermined state wherein this reference vector is assumed to be stable, this state preferably being detectable on the basis of observation components independent of the reference value.

It will also appear more generally to a person skilled in the art that various modifications can be made to the embodiments described above, in light of the teaching disclosed above. In the claims below, the terms used must not be interpreted as limiting the claims to the embodiment described in the present description, but must be interpreted so as to include all equivalents that the claims are intended to cover due to their wording and that can be envisaged by a person skilled in the art applying general knowledge to the implementation of the teaching disclosed above.

The invention claimed is:

1. A method for detecting activity of a physical system carrying a motion sensor, the method comprising:
   obtaining a reference value ($\hat{\lambda}$) of a vector representing a reference axis that indicates a preferred direction;
   extracting a time sequence of measurements provided by the motion sensor;
   deducing therefrom a time observation sequence calculated using the time sequence of measurements, at least one component of the time observation sequence being calculated from the time sequence of measurements using the obtained reference value ($\hat{\lambda}$);
   using a statistical model of components of the time observation sequence in view of a plurality of possible predetermined states of the physical system, determining the activity of the physical system in the form of a time sequence of states corresponding to the time observation sequence; $\hat{\lambda}$
   determining whether a calibration is needed by
      calculating a likelihood value for the time observation sequence in view of said statistical model, and
      comparing said likelihood value with a predetermined threshold (δ); and
   on the basis of the comparison, performing the calibration, in response to determining that the calibration is needed, by updating the obtained reference value ($\hat{\lambda}$).

2. The detection method as claimed in claim 1, wherein the reference axis is estimated, via its representative vector, with measurements provided by the motion sensor.

3. The detection method as claimed in claim 1, further comprising invalidating at least some of the time sequence of states corresponding to the time observation sequence, on the basis of the likelihood value.

4. The detection method as claimed in claim 1, wherein the time observation sequence is deduced from the time sequence of measurements by
   calculating a first component, on the basis of a low-pass filtering with a predetermined cutoff frequency of each component of the time sequence of measurements, then projecting the resulting components onto the reference value $\hat{\lambda}$ ($\hat{\lambda}$); and calculating at least one second component, on the basis of a band-pass filtering with predetermined cutoff frequencies of each component of the time sequence of measurements.

5. The detection method as claimed in claim 1, wherein the statistical model is a single Markov model with hidden states, each hidden state of which corresponds to one of the possible predetermined states of the physical system, the law of conditional probability of the observation of each hidden state being modeled by a sum of normal laws.

6. The detection method as claimed in claim 1, wherein the calibration comprises:
calculating the likelihood value for the time observation sequence in view of said statistical model in the form:

$$V = \frac{1}{N} \log(p(O_{1:N})),$$

where N is the number of observation samples in the time observation sequence (O), $O_{1:N}$ designating the N successive samples and $p(O_{1:N})$ the probability thereof;
comparing said likelihood value with a predetermined threshold ($\delta$), said threshold being defined on the basis of the random drawing of a plurality of theoretical time observation sequences based on said statistical model; and
activating the estimation of a new reference value ($\hat{\lambda}$) for the vector representing the reference axis only if the likelihood value is lower than the predetermined threshold ($\delta$).

7. The detection method as claimed in claim 1, wherein:
at least one component of the time observation sequence is calculated independently of the reference value ($\hat{\lambda}$) of the vector representing the reference axis,
at least one state of the physical system corresponding to a time sequence measurement is detected on the basis of the time observation sequence component independent of the reference value ($\hat{\lambda}$), and
the updated reference value ($\hat{\lambda}$) is estimated on the basis of the time sequence measurement corresponding to the state detectable on the basis of the time observation sequence component independent of the reference value ($\hat{\lambda}$).

8. The detection method as claimed in claim 7, wherein updating the obtained reference value ($\hat{\lambda}$) of the vector representing the reference axis comprises:
detecting and recovering, on the basis of said at least one time observation sequence component independent of the reference value ($\hat{\lambda}$), a time sequence measurement corresponding to a predetermined state wherein the vector representing the reference axis must have, on average, the reference value in consideration of said statistical model;
calculating the average values of the components of said representative vector in the time sequence measurement corresponding to the predetermined state, by low-pass filtering with a predetermined cutoff frequency of each component of the time sequence measurement, then calculating average values of the filtered components; and
assigning the average values to the updated reference value.

9. The detection method as claimed in claim 1, wherein the plurality of possible predetermined states include: a "sitting position" state, a "sitting/standing transition" state, a "static standing position" state, a "walking" state and a "standing/sitting transition" state, and
the reference value ($\hat{\lambda}$) is the value, in the frame of the measurement axes of a three-dimensional accelerometer, of the components of a vertical downward-oriented unit vector when a person being observed is wearing the three-dimensional accelerometer and is in the "static standing position" or "walking" state.

10. A device for detecting activity of a physical system, the device comprising:
a motion sensor configured to be carried by the physical system to provide a time sequence of measurements;
a memory configured to store a statistical model associating possible values of components of a time observation sequence with a plurality of possible predetermined states of the physical system; and
processing circuitry, connected to the motion sensor and to the memory, programmed to
obtain a reference value ($\hat{\lambda}$) of a vector representing a reference axis that indicates a preferred direction,
calculate a time observation sequence on the basis of the time sequence of measurements, at least one component of the time observation sequence being calculated from the time sequence of measurements using the obtained reference value ($\hat{\lambda}$),
determine, using the statistical model, the activity of the physical system in the form of a time sequence of states corresponding to the time observation sequence,
calculate a likelihood value for the time observation sequence in view of said statistical model,
compare the likelihood value with a predetermined threshold ($\delta$), and
perform a calibration of the device by updating the obtained reference value ($\hat{\lambda}$) on the basis of the comparison.

11. The detection device as claimed in claim 10, wherein the motion sensor is an accelerometer with three measurement axes, the reference axis estimable by the time sequence of measurements provided by the motion sensor being the axis of the earth's gravitational field, the reference value ($\hat{\lambda}$) of a vector representing the axis being calculated on the basis of an estimation of the coordinates of an acceleration due to the earth's gravitational field in the frame of reference of the measurement axes of the accelerometer when the physical system is in a predetermined state.

12. A system for detecting the activity of a physical system, comprising:
a belt to be worn on a torso or a waist of a person, and
a housing secured to the belt and comprising the detection device as claimed in claim 10.

13. A non-transitory computer-readable storage medium including computer executable instructions, wherein the instructions, when executed by a computer, cause the computer to perform a method for detecting activity of a physical system carrying a motion sensor, the method comprising:
obtaining a reference value ($\hat{\lambda}$) of a vector representing a reference axis that indicates a preferred direction;
extracting a time sequence of measurements provided by the motion sensor;
deducing therefrom a time observation sequence calculated using the time sequence of measurements, at least one component of the time observation sequence being calculated from the time sequence of measurements using the obtained reference value ($\hat{\lambda}$);
using a statistical model of components of the time observation sequence in view of a plurality of possible predetermined states of the physical system, determining the activity of the physical system in the form of a time sequence of states corresponding to the time observation sequence;

determining whether a calibration is needed by
- calculating a likelihood value for the time observation sequence in view of the statistical model, and
- comparing the likelihood value with a predetermined threshold ($\delta$), and on the basis of the comparison, performing the calibration, in response to determining that the calibration is needed, by updating the obtained reference value ($\hat{\lambda}$).

* * * * *